United States Patent [19]
Holmberg

[11] Patent Number: 5,786,214
[45] Date of Patent: Jul. 28, 1998

[54] PH-SENSITIVE IMMUNOLIPOSOMES AND METHOD OF GENE DELIVERY TO THE MAMMALIAN CENTRAL NERVOUS SYSTEM

[75] Inventor: Eric G. Holmberg, Eagle River, Ak.

[73] Assignee: Spinal Cord Society, Fergus Falls, Minn.

[21] Appl. No.: 356,703

[22] Filed: Dec. 15, 1994

[51] Int. Cl.$^6$ ............ C12N 15/63; C12N 15/85; C12N 15/88

[52] U.S. Cl. .............. 435/375; 435/6; 435/69.1; 435/172.1; 435/172.3; 424/9.321; 424/450; 424/131.1; 424/152.1; 514/44

[58] Field of Search ............. 514/44; 424/9.321, 424/9.322, 450; 435/72.3, 6, 69.1, 70.1, 320.1, 375; 935/22, 33, 34, 36, 54, 55, 56

[56] References Cited

U.S. PATENT DOCUMENTS

| | | | |
|---|---|---|---|
| 4,089,801 | 5/1978 | Schneider | 252/316 |
| 4,675,310 | 6/1987 | Chapman et al. | 514/6 |
| 4,693,994 | 9/1987 | McCutchan et al. | 514/15 |
| 4,707,357 | 11/1987 | Dame et al. | 424/88 |
| 4,708,933 | 11/1987 | Huang et al. | 435/7 |
| 4,789,633 | 12/1988 | Huang et al. | 435/240 |
| 4,863,717 | 9/1989 | Keana | 424/9 |
| 4,906,476 | 3/1990 | Radhakrishman | 424/450 |
| 4,925,661 | 5/1990 | Huang | 424/85 |
| 4,957,735 | 9/1990 | Huang . | |
| 4,959,353 | 9/1990 | Brown et al. | 514/12 |
| 5,049,388 | 9/1991 | Knight et al. | 424/450 |
| 5,049,389 | 9/1991 | Radhakrishman | 424/450 |
| 5,059,421 | 10/1991 | Loughrey et al. | 424/417 |
| 5,092,841 | 3/1992 | Spears | 604/96 |
| 5,100,662 | 3/1992 | Bolcsak et al. | 424/88 |
| 5,135,737 | 8/1992 | Keana | 424/9 |
| 5,137,720 | 8/1992 | Gangemi et al. | 424/85 |
| 5,198,224 | 3/1993 | Ono et al. | 424/450 |
| 5,199,951 | 4/1993 | Spears | 604/96 |
| 5,283,185 | 2/1994 | Epand et al. | 435/172.3 |
| 5,428,132 | 6/1995 | Hirsch et al. | 530/387.1 |

OTHER PUBLICATIONS ph-Sensitive and Target Sensitive Immunoliposomes for Drug Targeting. Eric C. Holmberg & Leaf Huang. Liposomes in the Therapy of Infectious Diseases and Cancer. 1989. pp. 25–34.

A Rapid Alkaline Extraction Procedure for Screening Recombinant Plasmid DNA. H.C. Birnboim and J. Doly. Nucleic Aids Research, vol. 7, No. 6., 1979. pp. 1513–1523.

A Monoclonal Antibody Detaches Embryonic Skeletal Muscle from Extracellular Matrices. N. T. Neff, C. Lowrey et al. Journal of Cell Biology, vol. 95. Nov. 1992. pp. 654–666.

Antibody Directed Lipsomes as Drug Delivery Vehicles. Stephen Wright & Leaf Huang. Advanced Drug Delivery, Rev. 3, 1989 pp. 343–389.

Monoclonal Antibody Targetin of Liposomes to Mouse Lung in Vivo. Brenda J. Hughes, Stephen Kennel et al. Cancer Research 49. Nov. 15, 1989, pp. 6214–6220.

Structural and Functional Comparisons of pH-sensitive liposomes composed of phosphatidylethanolamine and Three Different Diacylsuccinylglycerols. David Collins, David C. Litzinger, Leaf Huang. Bioschimica et Biophysica Acta, 1990. pp. 234–242.

Characterization of in Vivo Immunoliposome Targeting to Pulmonary Endothelium. Kazuo Maruyama, Eric Holmberg, et al. Journal of Pharmaceutical Sciences, vol. 79, No. 11. Nov. 1990. pp. 978–984.

Highly Efficient Immunoliposomes Prepared with a Method Which Is Compatible with Various Lipid Compositions. Eric Holmberg, Kazuo Maruyama et al. Biochemical & Biophysical Research Communications, vol. 165, No. 3, Dec. 29, 1989, pp. 1272–1278.

ph-Sensitive Immunoliposomes as an Efficient and Target-Specific Carrier for Antitunor Drugs. Jerome Connor and Leaf Huang. Cancer Research, vol. 46. Jul. 1986. pp. 3431–3435.

Cytotoxicity of Diphtheria Toxin A Fragment to Toxin-Resistant Murine Cells Delivered by pH-Sensitive Immunoliposomes. David Collins and Leaf Huang. Cancer Research. vol. 47. Feb. 1, 1987. pp. 735–739.

Lipid Polymorphism and the Functional Roles of Lipids in Biological Membranes. P.R. Cullis and B. De Kruijff. Biochimica et Biophysica Acta, vol. 599, 1979. pp. 339–420.

C. Wang et al. PNAS 84 (Nov. 1987) 7851–5.

K. Suda et al. Neuro Report 5 (14) ('94) 1749–51 (Abstract).

E. Holmberg et al. BBRC 201(2) (194) 888–93 (Abstract).

Y. Takamiya et al. J. Neurosurgery 79(1) (93) 104–110 (Abstract).

E. Daneiger et al. PNAS 86(21) (89) 8565–69 (Abst.).

R. Fabian Neurology 40 (3 Pz. 1) (90) 419–22 (Abst).

B. Niggeman et al. Neurosci. Let I. 51(2) (84) 231–4 (Abst.).

E. Daneiger et al. PNAS 86: 8565–9 ('89).

Y. Takamiya J. Neurosurg. 79: 104–110 ('93).

R. Fabian Neurology 40:419–22 ('90).

B. Niggeman Neurosci. Lett. 51:231–4 ('84).

H. San et al. Human Gene Therapy 4:781–8 ('93).

P. Hug et al. B. B. Acta 1097:177 ('91).

P. Felgner et al. PNAS 84:7413–17 ('87).

J. Felgner et al. J.B.C. 269(4) 2550–61 ('94).

M. Schappe et al. Cancer Res. 51(18):4986–93 ('91).

E. Geisert et al. Neurosci. Lett. 133(2)262–6 ('91).

I. Solodin et al. Biochem. 34:13537–44 ('95).

E. Holmberg, et al., *Journal of Lipsome Research* 1(4) (1990), pp. 393–406.

Primary Examiner—Charles C. P. Rories
Attorney, Agent, or Firm—Palmatier, Sjoquist, Voigt & Christensen, P.A.

[57] ABSTRACT

This invention relates to pH-sensitive immunoliposomes with a conjugated antibody sensitive to cells of the mammalian CNS, a method for introducing genetic material into the cells of the mammalian CNS in vitro through these liposomes, and a method of introducing genetic material into the cells of the mammalian CNS through direct injection of the liposomes into the CNS.

22 Claims, 5 Drawing Sheets

PH-SENSITIVE IMMUNOLIPOSOMES AND METHOD OF GENE DELIVERY TO THE MAMMALIAN CENTRAL NERVOUS SYSTEM

BACKGROUND OF THE INVENTION

Much of the current spinal cord regeneration research is focused on manipulating the function of neurons or glia, in order to promote axon growth or remove the inhibition of axon growth. These studies are increasingly designed to specifically alter the function of a particular gene or genes. Usually, the procedure is to introduce a genetic element into the cells of interest, and either block or enhance the expression of an important gene product. Up to this time, almost all such efforts have been concentrated on cells in vitro, where it is possible to treat the entire dish as a single population of cells, and then assay for the desired effect in the cells of interest. The long term goal of many of these studies is to provide a remedy for paralysis in humans. Unfortunately, the "shotgun" approach of transforming cells nonspecifically with a therapeutic gene will never be a viable way of treating this problem in vivo. In fact, such attempts could have potentially devastating effects on the function of the nervous system of the recipient. It is clear that for the potentially important gene therapy studies now being conducted in vitro to have application in the treatment of paralysis in vivo, a method must be devised to selectively deliver such genes (or other therapeutic agents) to specific cell types within the CNS.

Encapsulation of therapeutic pharmaceutical and genetic products by a targetable vehicle has been a goal for many investigators for years. Many problems have been encountered along the way regarding the specificity, mode of action, and physiological response to the varied therapies tested. The natural occurrence of the components of a liposome, a microscopic hollow sphere or "balloon" made of two layers of specific combinations of lipid or fatty molecules, make it an ideal carrier for delivery of therapeutic molecules. It has been shown that both drugs and genes are able to be delivered specifically to cells in vitro and in vivo with the desired specific effect. (P. R. Cullis and B. Dekruijff. *Biochim. Biophy. Acta*, 559, 339 (1979); J. Connor and L. Huang, *Cancer Res.*, 46, 3431 (1986); and D. Collins and L. Huang, *Cancer Res.*, 47, 735 (1987)).

The delivery of the liposome is facilitated by the chemical coupling of a specific monoclonal antibody to the outside of the liposome so that it will only bind to the specific site that it is intended to bind to. Such constructs are called immunoliposomes. Since the first success with liposome therapies a series of advancements and setbacks have occurred. The targeting ability of liposomes to carry the intra-liposome contents to a specific site has been increased by a factor of >10 by the development of a series of techniques and antibody combinations used by Holmberg et al. (B. J. Hughes and S. Kennel, R. Lee and L. Huang, *Cancer Res.*, 49, 6214 (1989); K. Maruyama, E. Homberg, S. Kennel, A. Klibanov, V. Torchillin, and L. Huang, *J. Pharm. Sci.*, 79(11), 978 (1990); E. Holmberg, K. Maruyama, D. Litzinger, S. Wright, M. Davis, G. Kabalka, S. Kennel, and L. Huang, *Biochem. Biophys. Res. Comm.*, 165(3), 1271 (1989)).

A series of synthetic lipids have been synthesized to facilitate the intracellular delivery of the liposome's contents after the cell has engulfed the liposome. The normal endocytic pathway that a cell utilizes to engulf external particles will cause the digestion and destruction of the particle. In the case of an immunoliposome the liposome and the contents will be destroyed. The natural endocytic pathway involves a pH change in the endocytic particle, the endosome, by the addition of naturally occurring proton pumps after the cell has internalized the particle. This causes a drop in the pH of the internal portion of the endosome. This occurrence can be used to the advantage of the liposome engineer in that liposomes have been developed that "disrupt" when the pH is lowered to a certain point. The point at which a pH-sensitive immunoliposome "disrupts" can be controlled by the addition, to the components of the liposome, of a variety of lipids. (S. Wright and L. Huang, *Adv. Drug Delivery Rev.*, 3, 343–389 (1989); D. Collins, D. C. Litzinger, and L. Huang, *Bichim. Biophys. Acta*, 1025(2), 234–242 (1990)). The proper combination of components will allow the successful delivery of the liposomes contents to the cell in an intact fashion such that they are biologically active and effective.

Huang (U.S. Pat. No. 4,957,735) discloses target-sensitive immunoliposomes which bind to the cell surface for the delivery of cytotoxic drugs. However, Huang '735 does not disclose the use of pH-sensitive immunoliposomes for the delivery of genetic material to the interior of the cell, in order to transfect the cell. Furthermore, Huang '735 does not disclose target-sensitive immunoliposomes which are sensitive to cells of the mammalian CNS.

Huang (U.S. Pat. No. 4,925,661) discloses target-specific cytotoxic liposomes which are also pH-sensitive. However, Huang '661 does not disclose the delivery of genetic material by such liposomes, nor the targeting of such liposomes to the mammalian CNS.

Huang et.al. (U.S. Pat. No. 4,789,633) discloses pH-sensitive liposomes and their use for introducing DNA into the cells of animals by intravenous injection. However, this is a non-specific targeting by liposomes without a conjugated antibody. Huang '633 does not disclose the use of pH-sensitive immunoliposomes to specifically target cells of the mammalian CNS in vitro or in vivo.

Immunoliposome therapy has not achieved the success that was initially predicted. The major obstacles have been nonspecific uptake of lipids by the liver and the destruction of liposomes by the immune system. Both of these major problems are unique to the peripheral circulation and do not exist within the central nervous system. Therefore, although some important technical questions will still need to be addressed, there is a much greater probability that immunoliposome therapy can provide an excellent method for delivery of active agents to specific cell types via direct injection into the CNS.

There is a need for a pH-sensitive immunoliposome for the delivery of genetic material to the mammalian central nervous system (CNS). The immunoliposomes must be usable for gene delivery both in vitro and in vivo by direct injection into the CNS, in order to avoid the obstacles associated with the peripheral circulation.

SUMMARY OF THE INVENTION

This invention relates to pH-sensitive immunoliposomes with a conjugated antibody sensitive to cells of the mammalian CNS, a method for introducing genetic material into the cells of the mammalian CNS in vitro through these liposomes, and a method of introducing genetic material into the cells of the mammalian CNS through direct injection of the liposomes into the CNS.

A principal object and advantage of the present invention is that it allows the encapsulation of biologically-active agents into a delivery vehicle which achieves specific delivery to cells of the mammalian CNS, i.e., glia and neurons.

A second object and advantage of the present invention is that it allows specific transfection of mammalian CNS cells by exogenous genes.

A third object and advantage of the present invention is that it allows transfection of cells of the mammalian CNS by direct injection into the CNS of liposome-encapsulated genetic material. This has important implications for gene therapy of human paralysis.

A fourth object and advantage of the invention is that the liposomes may be targeted specifically at neurons or specifically at glia by conjugating the liposomes with an antibody specific to neurons or an antibody specific to glia.

DETAILED DESCRIPTION OF THE PREFERRED EMBODIMENTS

Materials: Lipids were obtained from Avanti Polar Lipids, Inc. (Alabaster, Ala.). 1-Ethyl-3 (3-dimethylaminopropyl) carbodiimide (EDC) and N-hydroxysulfosuccinimide (S-NHS) were obtained from Pierce (Rockford, Ill.). Cholesterol, oleic acid, and all other chemicals were obtained from Sigma Chemical Co. (St. Louis, Mo.). Lipofectin and Transfectase were obtained from Gibco Laboratories. (Grand Island, N.Y.).

Antibodies: The monoclonal antibody 13–21 was generated from a fusion of lymph nodes in which two mice were immunized with a preparation of external membrane and associated proteins produced from mixed primary cultures of rat cerebral cortex. Cells from the neonatal rat cortex were cultured using methods previously described (E.G. Holmberg and L. Huang, *Liposomes in the Therapy of Infectious Diseases and Cancer*, Alan R. Liss, Inc., 25–34 (1989)). Fragments of the external membrane of the cultured cells were prepared following the procedure described by Neff et al. (N. T. Neff, C. Lowery, C. Decker, A. Tovar, C. Damsky, Buck, and A. F. Horwitz, *J. Cell Biol*, 654–666 (1982)). Antibodies were tested using an immunoblot analysis. Two subclasses of antibodies were determined. 5–113 was IgM subclass and 13–21 was IgG subclass, and both were used as targeting ligands. Both monoclonal antibodies were determined to be glia specific via indirect immunofluorescence staining. THY 1.1 monoclonal antibody was produced using a cell line purchased from American Type Culture Collection (ATTC TIB 100). Non-immune IgM was purchased from ICN (Irvine, Calif.).

Immunoliposome Preparation: N-glutaryl-phosphatidylethanolamine (NGPE) dissolved in $CHCl_3$ was dried with $N_2$ gas, and solubilized with octylglucoside in MES Buffer to a final concentration of 824 mg/ml (NGPE to octylglucoside molar ratio=0.07). Forty ul 1-ethyl-3-(3-dimethylaminopropyl) carbodiimide (0.25M in MES buffer) and 40 ul N-hydroxysulfosuccinimide (0.1M in MES buffer) were added to 200 ul of above NGPE solution and then incubated for 10 min. at room temperature. The mixture was neutralized by adding HEPES buffer (100 mM, pH 7.5) and 1N NaOH to pH 7.5. Monoclonal antibody 34A and a trace amount of $^{128}$I-labeled antibody were then added, and incubated for 8 hr. at 4° C. with gentle stirring. Lipid mixtures and trace amounts of $^{111}$In-DTPA-SA were mixed and evaporated free of organic solvent with $N_2$ gas. The dried lipid film was vacuum desiccated and solubilized with octylglucoside (100 mM in PBS (pH 7.4), lipid:octylglucoside=1:5, m/m). The resultant solution was mixed vigorously with the antibody conjugated with NGPE, and then the detergent was removed by dialysis in PBS for 12–18 hr at 4° C. The immunoliposomes were extruded 4 times through a 0.4 um nucleopore membrane. The size of liposomes was measured using a Coulter N4SD sub-micron particle size analyzer (Hialeah, Fla.). The immunoliposomes were separated from the unbound antibody on a Bio-Gel A 1.5M (Bio-Rad) column. Peak liposome fractions were collected and diluted to 1 mg lipid/ml PBS (pH 7.4). Plasmid DNA was added and the entire mixture was dialyzed for 48 hours at 4° C. in the final step. After dialysis, liposomes were sized four times through a 0.4 um Nuclepore membrane.

Liposomes were separated from free plasmid DNA and unconjugated antibody on a BioGel A 1.5M (Bio-Rad) column. Liposomes were diluted to a concentration of 1 mg/ml total lipid. Plasmid DNA and antibody concentrations were determined to be 0.025 mg/ml and 0.25 mg/ml, respectively, in the standard 1 mg/ml total lipid immunoliposome solution.

Plasmid Preparation: A DNA plasmid containing the marker gene B-galactosidase was obtained from Promega Corp. (Madison, Wis.). The plasmid expression was under the control of either the SV40 early promotor or the cytomegalovirus promotor. The plasmid DNA was amplified in *E. coli* DH5-alph cells and recovered by alkaline extraction. (H. C. Bimboim and J. Doly, *Nuc. Acids Res.*, 7, 1513 (1979)). Plasmid was purified by passage through Quiagen columns. (Quiagen Inc., Chatsworth, Calif.). Cell Culture Assay: NIH 3T3 fibroblasts and C6 glioma cells were seeded in six well plates and allowed to grow 50%–75% confluency. Cells were rinsed with serum free media and allowed to equilibrate. Liposomes were added to the cells and gently rocked for 1 hour. Experiments designed to test the specificity of the liposomes transfection necessitated the addition of free antibody to the cell cultures prior to the addition of the immunoliposomes. After 1 hour of exposure to the free antibody, the cells were rinsed and immunoliposomes were added in serum free media with mild agitation. After rocking, the cells were rinsed and serum-containing media was added and cells were incubated at 37° C. in 5% $CO_2$ for 48 hours. Treated cells were rinsed and lightly fixed in 3% paraformaldehyde. Fixed cells were treated with X-gal as previously described. (K. Lin and C. B. Chai, Biotechniques, 7:576 (1989)). Cells expressing B-galactosidase appear blue after the addition of X-gal. Cells were microscopically examined and counted with transformed cells expressed as a percent of the total cell population. Data were determined to be statistically significant using a students' t-test.

Immunoliposomes were constructed using antibodies 5–113 and 13–21, which bind specifically to glial cells, and containing a B-galactosidase expressing gene. Bare liposomes, containing plasmid but with no attached targeting antibody, were constructed as a control for immunoliposomes. To compare the efficiency of immunoliposome transfection with other commercially available methods, cells were transfected using lipofectin and transfectase. Cells were also exposed to an aliquot of free plasmid.

Figure 1:
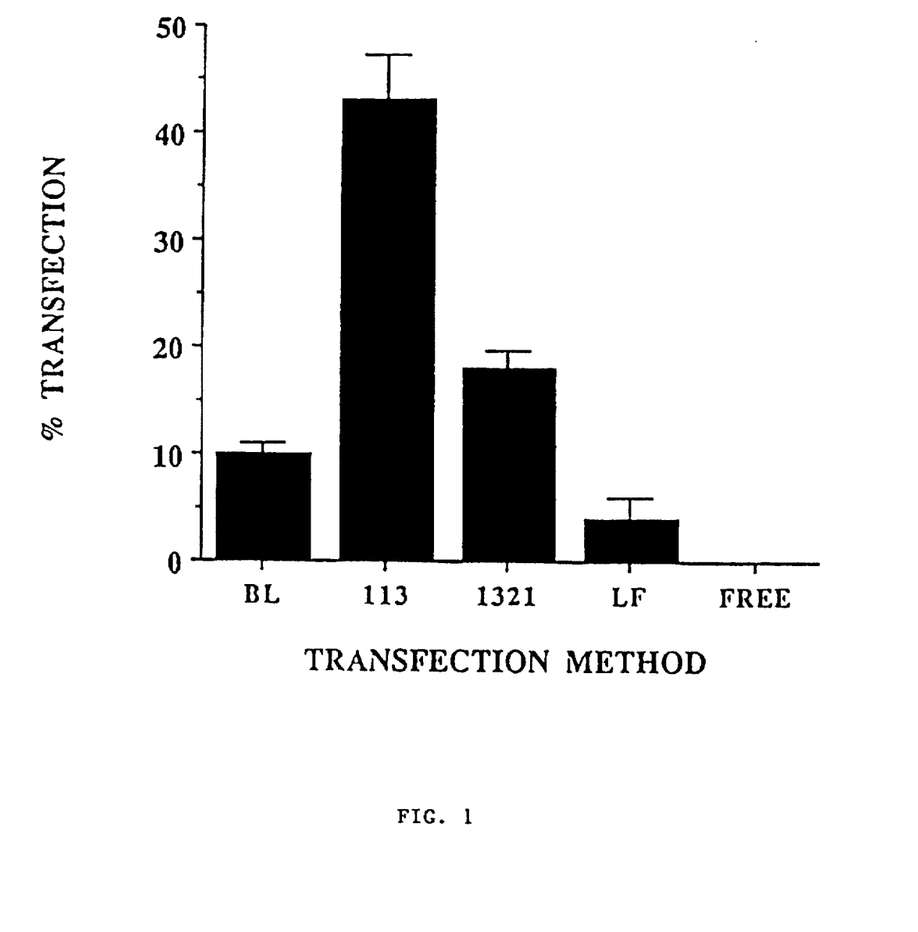
FIG. 1: 15 ul of liposomes (1 mg/ml total lipid, 0.25 mg/ml antibody, 0.025 mg/ml plasmid DNA) were added to C6 glioma cells at 75% confluence. After exposure to immunoliposomes cells were fixed and assayed for expression of B-galactosidase. Transformed cells were counted and are expressed as a function of the percent total cell population±S.D. (n=3). (BL) bare liposomes, (113) 5–113 immunoliposomes, (1321) 13–21 immunoliposomes, (LF) lipofectin, (FREE) free plasmid. Free plasmid transfection had less than 1% transfection.

FIG. 1 illustrates the percent of transfected cells versus the transfection method for C6 glioma cells. Results in FIG. 1 indicate that maximal transfection occurred when cells were exposed to immunoliposomes with conjugated antibody 5–113 when identical concentrations (10 ug lipid/well of cells, 75% confluent) of immunoliposomes were added to the cells. The transfection rate was 43.7±4.2% (n=3) as determined by differential cell counting. A smaller percentage of cells were transfected when exposed to 13–21 conjugated immunoliposomes, 18.1±1.5% (n=3) of the cells were transformed. Background transfection via liposomes is quantified by the addition of bare liposomes. The transfection efficiency for bare liposomes was 10.2±0.9% (n=3).

C6 Glioma cells were transfected via two commercially available methods and by the addition of free plasmid. Results indicate a transfection rate of 4.3±2.1% (n=3) with lipofectin. No detectable transfection was observed when cells were transfected with Transfectase or free plasmid. (Data not shown for Transfectase)

Figure 2:
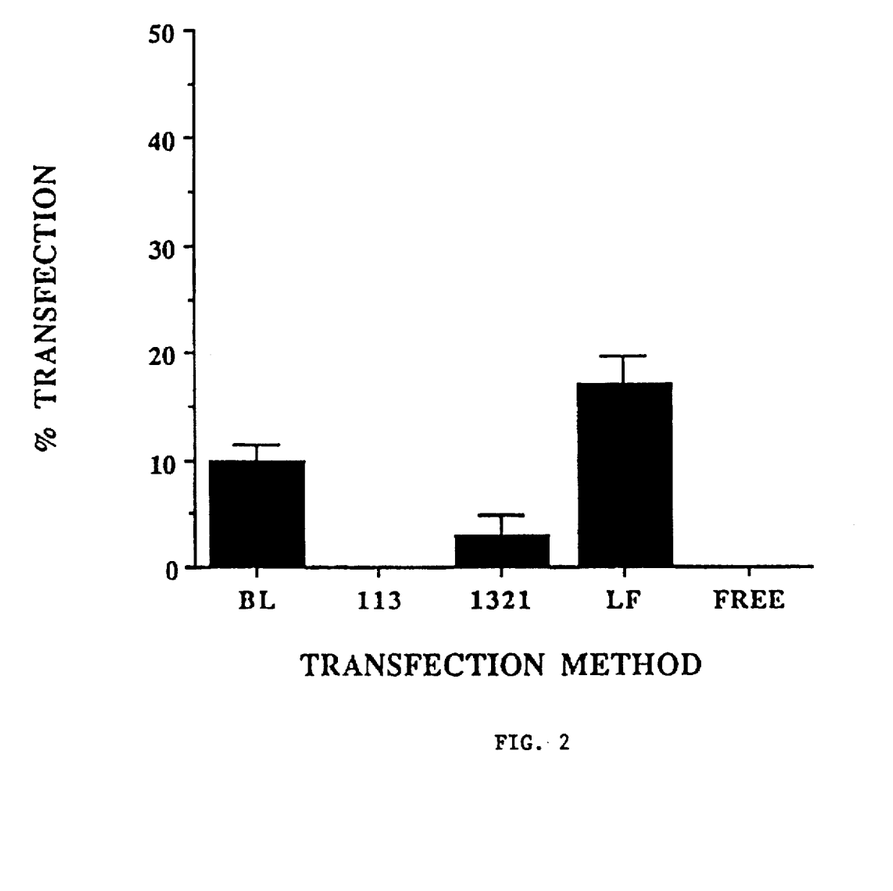
FIG. 2: 15 ul of liposomes (1 mg/ml total lipid, 0.25 mg/ml antibody, 0.025 mg/ml plasmid DNA) were added to NIH 3T3 cells at 75% confluence. After exposure to immunoliposomes cells were fixed and assayed for expression of B-Galactosidase. Transformed cells were counted and are expressed as a function of the percent total cell population±S.D. (n=3). (BL) bare liposomes, (113) 5–113 immunoliposomes, (1321) 13–21 immunoliposomes, (LF) lipofectin, (FREE) free plasmid. 113 and free plasmid transfection had less than 1% transfection.

To examine the transfection specificity to cell type of 5–113 and 13–21 immunoliposomes, NIH 3T3 fibroblasts were exposed via the above mentioned transfection methods. FIG. 2 illustrates the percentage of cells transfected versus the transfection method. Maximal transfection occurred when lipofectin was used as a transfection carrier. 17.4±2.6% (n=3) transfection efficiency was observed. Results with bare liposomes indicate a transfection frequency of 10.1±1.5% (n=3), a rate nearly identical to that of the C6 glioma cells. No detectable transfection was observed when cells were exposed to transfectase (data not shown), free plasmid, or 5–113 immunoliposomes. A very low transfection rate, 3.1±1.7% (n=3) was observed when 3T3 cells were exposed to 13–21 immunoliposomes.

Figure 3:
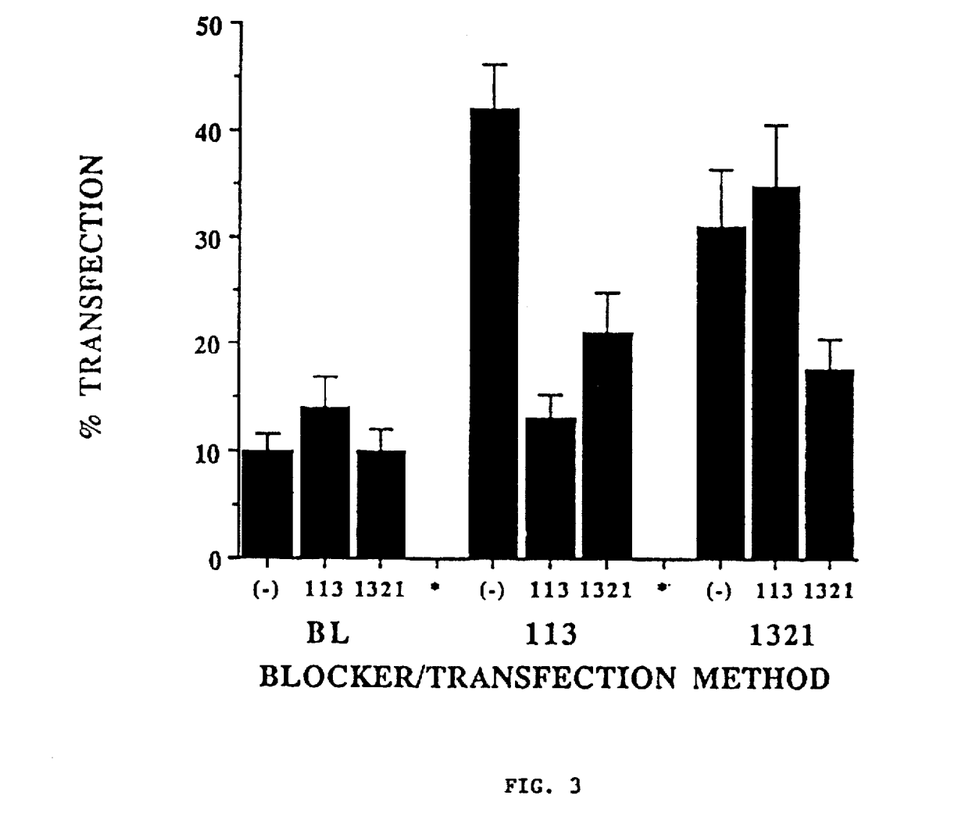
FIG. 3: C6 glioma cells were presaturated with antibodies 5–113 (113), 13–21 (1321), and control buffer (–) at 4° C. prior to exposure to bare liposomes (BL), 5–113 immunoliposomes (113), and 13–21 immunoliposomes at 37° C. to block specific binding sites located on the cell surface prior to transfection. Blockers are smaller case and transfection liposomes are large case characters. Transformed cells were counted and are expressed as a function of the percent total cell population±S.D. (n=3).

To test the specificity of transfection, via immunoliposomes, cells were presaturated with free antibody prior to exposure to the immunoliposomes. Presaturation of the cell-surface antigens should block specific sites and reduce the specific binding to approximately background levels. FIG. 3 illustrates the percent of transformed C6 glioma cells versus transfection vehicle when cells were presaturated by either specific antibody or with the addition of no antibody. Little variation in background transfection levels was observed for the addition of plasmid containing bare liposomes with or without the prior addition of free antibody.

Antibody 5–113 immunoliposomes were added to C6 glioma cells in culture with and without the presaturation by either antibody. A transfection level of 42.8±4.2% (n=3) was observed with the addition of 5–113 immunoliposomes. Transfection levels were reduced three fold with the prior addition of 5–13 free antibody (13.2±2.2%, n=3) to the cells. Transfection levels were reduced approximately twofold with the prior addition of antibody 13–21 (22.1±3.91%, n=3) when 5–113 immunoliposomes were added to the cells. 13–21 immunoliposomes were added to C6 glioma cells and had a transfection efficiency of 31.7±5.39% (n=3). 13–21 immunoliposomes were added to C6 glioma with and without prior treatment of antibodies 13–21 and 5–113. Prior saturation of the cells with antibody 5113 resulted in a slight, but insignificant (P<0.50), increase in transfection 34.7±5.91% (n=3). Presaturation of the cells with antibody 13–21 prior to addition of 13–21 immunoliposomes resulted in an approximate 40% decrease in transfection efficiency to 17.1±2.7% (n=3).

In vivo experiments

Figures 4, 5, 6:
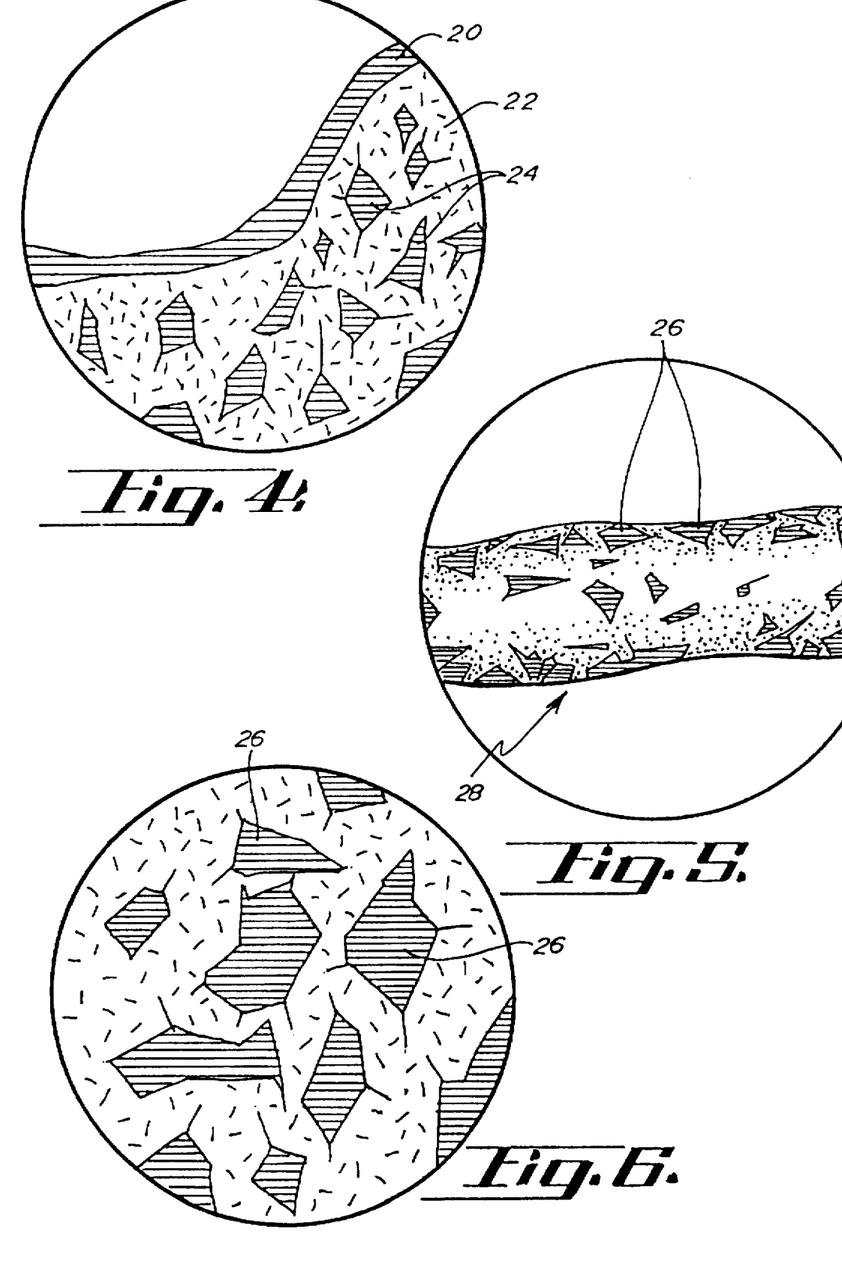
FIG. 4: A drawing of a photomicrograph taken from injections of 5–113 immunoliposomes into a cannula-implanted brain lesion shows heavy labeling of the ependyma and glial scar. Most labeled cells appear to have an astrocyte morphology.
FIG. 5: Drawing of a low magnification photomicrograph of a longitudinal section of the spinal cord of a rat injected with THY 1.1 immunoliposomes. Dark colored cells are cells that react positively to the X-gal reaction indicating the expression of beta-galactosidase.
FIG. 6: Drawing of a high magnification photomicrograph of the section described in FIG. 5.

In Vivo experiments were conducted using four different types of immunoliposomes. Plasmid containing 5–113 immunoliposomes were directed at glia, plasmid containing THY 1.1 were directed to neuronal cells, and plasmid containing non-immune IgM immunoliposomes and bare liposomes acted as control vehicles. Two different experimental models were used to demonstrate the effectiveness of In Vivo gene delivery by injection directly into the CNS. The first model was composed of rats previously injured by a scalpel blade wound through the cerebral cortex, the internal capsule and the fimbria, to test delivery to the brain. The lesion was implanted with a cannula for future liposome delivery. Injections directly into the spinal cord of uninjured, healthy Sprague-Dawley rats composed the second model. Injections into the brain 5–113 immunoliposomes and non-immune IgM immunoliposomes were tested in chronically injured rat brains. As shown in FIG. 4, 5–113 immunoliposomes caused intense labeling of the gliotic scar 20 and the surrounding tissue 22 of the injection site. Most of these cells 24 observed to have color had astrocytic morphology, indicating that they are glia. In contrast, non-immune IgM immunoliposomes caused only light and diffuse labeling. This intense labeling of 5-113 immunoliposomes in comparison to non-immune IgM immunoliposomes indicates an increased transfection rate, due to the presence of the 5-113 antibody.

There was some non-specific labeling of pericytes and cells of choroid plexus observed with all injections. Light and diffuse labeling of ependymal cells was observed with non-immune IgM immunoliposomes along with some of the tissue adjacent to the ventricular system. However, this background labeling was of significantly less intensity than that observed with the 5-113 immunoliposomes.

Tissues taken from animals injected with non-immune IgG immunoliposomes or bare liposomes showed weak labeling of the cells at the injection site. Small numbers of both neurons and glia were observed as being labeled at this site. This observation was not seen in sham injected control animals, indicating that some minimal transfection occurs through liposomes without antibody.

Injections into the spinal cord

THY 1.1 immunoliposomes, which contain an antibody specific to an antigen expressed on the surface of neurons, were tested in the spinal cords of normal rats. As shown in FIGS. 5 and 6, the highest level of transfection was observed when THY 1.1 immunoliposomes were injected. The distinguishing feature of the THY 1.1 immunoliposomes was the increased number of transfected neurons 26 within the gray matter of the spinal cord 28, as compared to control experiments.

In all cases the heaviest labeling was observed at the injection site. Specificity of transfection was low at the injection site in that both cells of astrocytic and neuronal morphology were positive to the X-gal reaction. This is thought to be caused by the high concentration of liposomes and high hydrostatic pressure at the injection site. However, with the non-immune liposomes, the labeling of glial-like cells faded within a centimeter of the injection site and neurons were only labeled within 2 to 3 mm of the injection site. In contrast, with the THY 1.1 immunoliposomes, neurons 26 over the entire length of the spinal cord 28 were transfected. The intensity of the X-gal reaction product was the highest within 5 mm of the injection site; however, the neurons 26 within the spinal chord 28 were labeled from the sacral through the cervical levels of the chord. This indicates that the immunoliposomes were not destroyed by the immune system at the site of injection, but rather were able to transfect CNS cells at considerable distances from the injection site.

Figure 7:
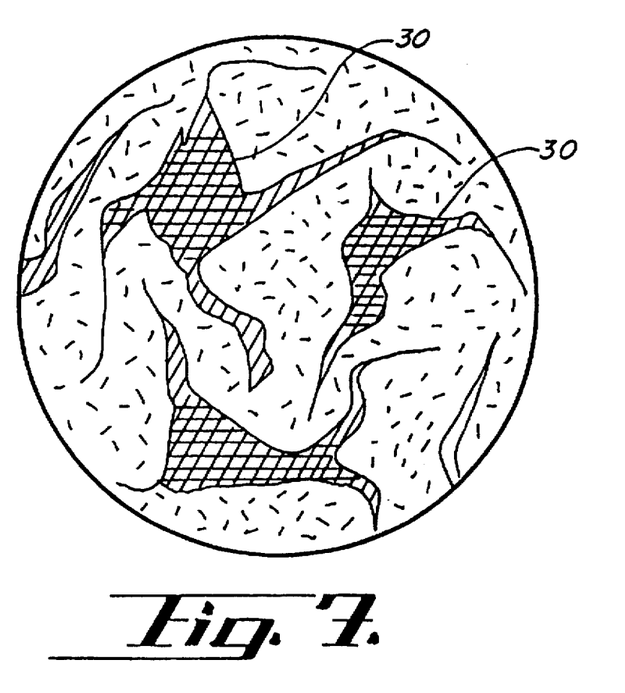
FIG. 7: Drawing of a high magnification photomicrograph similar to FIG. 6 with the exception of additional staining by TuJ1, an indicator of neuronal tubulin. Cells that contain both brown and blue colorings indicate neurons that have been successfully transfected via THY 1.1 immunoliposomes.
Figure 8:
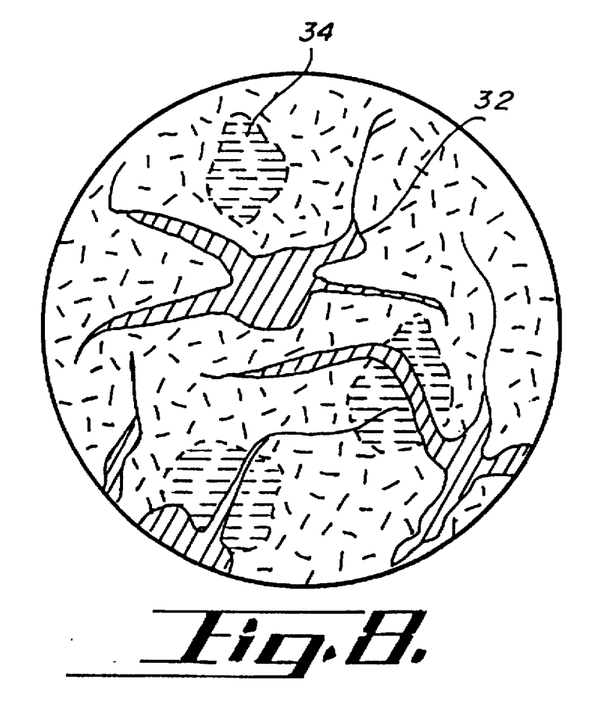
FIG. 8: Drawing of a photomicrograph of a section of white matter after transfection using THY 1.1 immunoliposomes. Blue cells indicate cells that have been successfully transfected via immunoliposomes and brown counter staining arises from the addition of glial fibrillary acid protein to indicate astrocytic cells. There appears to be very little cross-transfection between cell types.

In order to examine the specific morphology of the transfected cells, tissue sections were cross-stained with markers for both glia and neurons. Spinal cords were injected with THY 1.1 immunoliposomes containing a beta-galactosidase plasmid. Tissue sections were examined for labeling from X-gal. A large number of cells were observed to be X-gal positive in these sections. In order to determine the specific cell type of these cells similar sections were examined for their reactivity with TuJ1, a label for neuronal tubulin. As can be seen in FIG. 7, the cell bodies of the cells 30 positive for TuJ1 (shown by brown staining) are also positive for the X-gal reaction (shown by blue staining). This indicates that neurons are transfected by THY 1.1 immunoliposomes. A similar section was cross-stained with glial fibrillary acidic protein, GFAP. As can be seen in FIG. 8, the cell bodies of the cells 32 positive for GFAP (shown by brown staining) were not also positive for the X-gal reaction, and the cells 34 positive for the X-gal reaction (shown by blue staining) are not also positive for GFAP. The indications are that there is a heightened degree of transfection of neurons using the THY 1.1 immunoliposomes, and that the transfection can be used to transfect neurons without simultaneously transfecting glia.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. PH-sensitive immunoliposomes conjugated to an antibody specific to cells of the mammalian central nervous system, said liposomes consisting essentially of N-glutarylphosphatidylethanolamine, cholesterol, and oleic acid, said liposomes containing an entrapped DNA molecule encoding a polypeptide, for delivery of said DNA molecule to said cells by direct injection into the central nervous system, said liposomes having a lipid to antibody ratio of about 1 to 4, said liposomes being of a size less than or equal to about 0.4 um.

2. The pH-sensitive immunoliposomes of claim 1, wherein the antibody is specific to neuroglia.

3. The pH-sensitive immunoliposomes of claim 2, wherein said antibody is a monoclonal antibody.

4. The pH-sensitive immunoliposomes of claim 3, wherein said antibody is of the IgG subclass.

5. The pH-sensitive immunoliposomes of claim 3, wherein said antibody is of the IgM subclass.

6. The pH-sensitive immunoliposomes of claim 1, wherein said DNA molecule is a comprises a DNA plasmid.

7. The pH-sensitive immunoliposomes of claim 6, wherein said DNA plasmid contains the marker gene B-galactosidase.

8. The pH-sensitive immunoliposomes of claim 1, wherein the antibody is specific to neurons.

9. The pH-sensitive immunoliposomes of claim 8, wherein said antibody is a monoclonal antibody.

10. The pH-sensitive immunoliposomes of claim 9, wherein said antibody is the antibody THY 1.1.

11. A method for introducing DNA molecules encoding a polypeptide into cells of the mammalian central nervous system in vivo, comprising the steps of:

(a) preparing pH-sensitive immunoliposomes from N-glutarylphosphatidylethanolamine, cholesterol, and oleic acid and a conjugated antibody; having a lipid to antibody ratio of about 1 to 4; and being of a size less than or equal to about 0.4 um.

(b) entrapping DNA nolecules encoding a polypeptide in the pH-sensitive immunoliposomes; and (c) injecting the immunoliposomes directly into the mammalian central nervous system.

12. The method of claim 11, wherein said antibody is specific to neuroglia.

13. The method of claim 12, wherein said antibody is a monoclonal antibody.

14. The method of claim 13, wherein said antibody is of the IgG subclass.

15. The method of claim 13, wherein said antibody is of the IgM subclass.

16. The method of claim 11, wherein said DNA molecules are plasmids.

17. The method of claim 16, wherein said DNA plasmids contain the marker gene B-galactosidase.

18. The method of claim 11, wherein the antibody is specific to neurons.

19. The method of claim 18, wherein the antibody is a monoclonal antibody.

20. The method of claim 18, wherein the antibody is the antibody THY 1.1.

21. pH-sensitive immunoliposomes conjugated to an antibody specific to mammalian neuroglia, said liposomes consisting essentially of N-glutarylphosphatidylethanolamine, cholesterol, and oleic acid, said liposomes containing an entrapped DNA molecule encoding a polypeptide, said liposomes being adapted to deliver said DNA molecule to said cells, said liposomes having a lipid to antibody ratio of about 1 to 4, said liposomes being of a size less than or equal to about 0.4 um.

22. pH-sensitive immunoliposomes conjugated to an antibody specific to mammalian neurons, said liposomes consisting essentially of N-glutarylphosphatidylethanolamine, cholesterol, and oleic acid, said liposomes containing an entrapped DNA molecule encoding a polypeptide, said liposomes being adapted to deliver said DNA molecules to said cells, said liposomes having a lipid to antibody ratio of about 1 to 4, said liposomes being of a size less than or equal to about 0.4 um.

* * * * *

UNITED STATES PATENT AND TRADEMARK OFFICE
CERTIFICATE OF CORRECTION

PATENT NO. : 5,786,214
DATED : Jul. 28, 1998
INVENTOR(S) : Eric G. Holmberg

It is certified that error appears in the above-indentified patent and that said Letters Patent is hereby corrected as shown below:

col. 5, line 14: please delete the word "Birnboim" and insert in its place --Birnheim-- col. 5, line 16: please start a new paragraph with the phrase "Cell Culture Assay:"

col. 6, line 44: after "experiments" please insert --:-- col. 6, line 59: after "brain" please insert --:-- col. 7, line 18: after "cord" please insert --:-- col. 8, line 37: please delete "comprises a DNA"

Signed and Sealed this

Eleventh Day of July, 2000

Q. TODD DICKINSON

Attest:

Attesting Officer

Director of Patents and Trademarks